United States Patent
Christoph et al.

(10) Patent No.: US 6,660,774 B2
(45) Date of Patent: Dec. 9, 2003

(54) USE OF (+)-TRAMADOL, O-DEMETHYLTRAMADOL OR (+)-O-DEMETHYL-TRAMADOL, O-DESMETHYL-N-MONO-DESMETHYL-TRAMADOL OR (+)-O-DESMETHYL-N-MONO-DESMETHYLTRAMADOL

(75) Inventors: Thomas Christoph, Aachen (DE); Elmar Friderichs, Zehntweg (DE)

(73) Assignee: Gruenethal GmbH, Aachen (DE)

( * ) Notice: Subject to any disclaimer, the term of this patent is extended or adjusted under 35 U.S.C. 154(b) by 0 days.

(21) Appl. No.: 10/116,123

(22) Filed: Apr. 5, 2002

(65) Prior Publication Data

US 2003/0069314 A1 Apr. 10, 2003

Related U.S. Application Data

(63) Continuation of application No. PCT/EP00/09420, filed on Sep. 27, 2000.

(30) Foreign Application Priority Data

Oct. 5, 1999 (DE) .......................................... 199 47 747
Jun. 21, 2000 (DE) .......................................... 200 02 943

(51) Int. Cl.$^7$ ............................................ A61K 31/135
(52) U.S. Cl. ......................................................... 514/646
(58) Field of Search .......................................... 514/646

(56) References Cited

FOREIGN PATENT DOCUMENTS

| DE | 19601744 | 7/1997 |
|----|----------|--------|
| DE | 19601745 | 10/1997 |
| EP | 0534628 | 11/1996 |
| EP | 1005861 | 6/2000 |
| WO | WO 93/04675 | 3/1993 |
| WO | WO 93/15062 | 8/1993 |
| WO | WO 98/46216 | 10/1998 |

OTHER PUBLICATIONS

Wielbalck et al., "Sind Tramadol–Enantiomere für die postoperative Schmerztherapie besser geeignet als das Racemat?", Anaesthesist, 1998, vol. 47, pp. 387–394.

Primary Examiner—Phyllis G. Spivack
(74) Attorney, Agent, or Firm—Crowell & Moring LLP

(57) ABSTRACT

Method for the treatment of increased urinary urgency or urinary incontinence comprising administering (+)-tramadol, O-demethyltramadol, (+)-O-demethyltramadol, O-desmethyl-N-mono-desmethyltramadol, or (+)-O-desmethyl-N-mono-desmethyltramadol, as free bases and/or in the form of physiologically compatible salts, are disclosed.

8 Claims, No Drawings

USE OF (+)-TRAMADOL, O-DEMETHYLTRAMADOL OR (+)-O-DEMETHYL-TRAMADOL, O-DESMETHYL-N-MONO-DESMETHYL-TRAMADOL OR (+)-O-DESMETHYL-N-MONO-DESMETHYLTRAMADOL

CROSS REFERENCE TO RELATED APPLICATIONS

The present application is a continuation of international patent application no. PCT/EP00/09420, filed Sep. 20, 2000, designating the United States of America, the entire disclosure of which is incorporated herein by reference. Priority is claimed based on Federal Republic of Germany patent application nos. 199 47 747.7, filed Oct. 5, 1999 and 200 02 943.6, filed Feb. 21, 2000.

BACKGROUND OF THE INVENTION

The invention relates to the use of (+)-tramadol or 0-demethyltramadol, in particular (+)-O-demethyltramadol, O-desmethyl-N-mono-desmethyltramadol, in particular (+)-O-desmethyl-N-mono-desmethyltramadol as free bases and/or in the form of physiologically compatible salts for the production of a pharmaceutical preparation for the treatment of increased urinary urgency or urinary incontinence and to corresponding pharmaceutical preparations and to a method for the treatment of increased urinary urgency or urinary incontinence.

Urinary incontinence is the involuntary release of urine, which occurs in an uncontrolled manner when the pressure within the bladder exceeds the pressure required to seal the ureter. This may be caused, on the one hand, by increased internal bladder pressure (for example due to detrusor instability) resulting in urge incontinence and, on the other hand, by reduced sphincter pressure (for example after giving birth or surgical intervention) resulting in stress incontinence. The detrusor is the coarsely bundled, multilayer bladder wall musculature, contraction of which results in voiding of urine, while the sphincter is the muscle which closes the urethra. Mixed forms of these types of incontinence occur, as do so-called overflow incontinence (for example in cases of benign prostate hyperplasia) or reflex incontinence (for example after spinal cord damage). Further details in this connection may be found in Chutka, D. S. and Takahashi, P. Y., 1998, *Drugs* 560: 587–595.

Urinary urgency is the state of increased bladder muscle tension directed towards voiding of urine (micturition) as bladder capacity is approached (or exceeded). This tension acts as the micturition stimulus. Increased urinary urgency is taken in particular to mean the occurrence of premature or more frequent, sometimes even painful urinary urgency, going as far as urinary compulsion. This consequently results in distinctly more frequent micturition. Possible causes are bladder inflammation and neurogenic bladder dysfunction as well as vesical tuberculosis. However, not all causes have yet been explained.

Increased urinary urgency and urinary incontinence are extremely unpleasant and those suffering from these symptoms have a clear need to alleviate them for as long as possible.

Increased urinary urgency and in particular urinary incontinence are conventionally treated somatically with substances which are involved in the reflexes of the lower urinary tract (Wein, A. J., 1998, *Urology* 51 (Suppl. 21): 43–47). These are generally medicines which have an inhibitory action on the detrusor muscle, which is responsible for the pressure within the bladder. These medicines are, for example, parasympatholytics such as oxybutynin, propiverine or tolterodine, tricyclic antidepressants such as imipramine or muscle relaxants such as flavoxate. Other medicines which in particular increase the strength of the urethra or the neck of the bladder exhibit an affinity to α-adrenergic receptors such as ephedrine, to β-adrenergic receptors such as clenbuterol or are hormones such as oestradiol. Certain opioids, diarylmethylpiperazines and diarylmethylpiperidines are also described for this indication in WO 93/15062.

WO 98/46216 demonstrated for the first time that tramadol may also be used for the indications of increased urinary urgency and urinary incontinence. Tramadol ((1RS,2RS)-2-dimethylaminomethyl-1-(3-methoxyphenyl)cyclohexanol) is a racemate and a known centrally acting analgesic, which strongly inhibits pain without causing the side effects known for opioids (*J. Pharmacol. Exptl. Ther.* 267, 331 (1993)).

It must, however, be born in mind that, for the indications under consideration, drug therapy will generally be of very long duration and, unlike many situations in which analgesics are used, the affected individuals feel themselves to be in a very unpleasant, but not intolerable situation. Care must accordingly be taken in this case, still more than with analgesics, to avoid side effects—the affected individuals will not want to swap one evil for another.

Although tramadol exhibits much fewer side effects than opioids, the use of tramadol is associated with a few, sometimes unpleasant, dose-related side effects. Moreover, analgesic action is largely undesirable in the long-term treatment of urinary incontinence. Using tramadol racemate for this indication thus has disadvantages because, even though the racemate has an effect on bladder function even at relatively low doses, therapeutic dosages may cause unwanted side effects, especially in certain groups of patients.

SUMMARY AND DETAILED DESCRIPTION OF THE INVENTION

The object of the present invention was accordingly to identify substances which are helpful in the treatment of increased urinary urgency or urinary incontinence and which preferably simultaneously exhibit reduced side effects and less analgesic action than known from the prior art.

It has surprisingly now been found that (+)-tramadol possesses excellent effect on bladder function and is accordingly suitable for the treatment of such conditions and exhibits this action at considerably lower dosages than the racemate.

The present invention accordingly provides the use of (+)-tramadol as a free base and/or in the form of physiologically compatible salts for the production of a pharmaceutical preparation for the treatment of increased urinary urgency or urinary incontinence.

Tramadol is a racemate and consists of equal quantities of (+)- and (−)-enantiomers. It is known from analgesic use that the enantiomers of tramadol have a differing pharmaceutical profile from the racemate. The (+)-enantiomer is distinguished by an opiate-like analgesic action, which is stronger than that of tramadol, while distinct inhibition of noradrenaline reuptake is observed with the (−)-enantiomer. It has been proven for (+)- and (−)-tramadol that, depending upon the model, the two enantiomers mutually reinforce their action (Raffa, R. et al., 1993, *J. Pharmacol. Exptl. Ther.* 267:331). It is obvious to assume that the potent analgesic action of tramadol is based on this mutually dependent reinforcement of action.

Completely at variance with this experience from analgesic use, investigation of the separate enantiomers with regard to their effect on bladder function revealed a surprisingly different picture. (+)-Tramadol was not only distinctly more active than the racemate, but was even considerably more active than twice the dose of the racemate mixture of (+)- and (−)-tramadol used. It may, however, be concluded from this not only that (+)-tramadol is the actual active substance, but also that (−)-tramadol appears not only to be inactive but, in contrast with analgesic use in the racemate, even appears to inhibit the action of (+)-tramadol on bladder function.

Using (+)-tramadol thus has clear advantages over the prior art, namely using tramadol as a racemate (WO 98/46216), as it is possible to use considerably lower dosages of distinctly less than 50% of the dosage required for tramadol. Side effects are correspondingly reduced as (−)-tramadol also makes a contribution to these, in particular also to the analgesic action. Possible methods for producing (+)-tramadol are described in *Arzneim. -Forsch./Drug Res.* 28 (I), 114 (1978) and in particular preferably in DE 196 01 745 C1.

When using (+)-tramadol, it is not necessary, but is preferred, to use solely the (+)-tramadol enantiomer. A smaller proportion of (−)-tramadol relative to the (+)-tramadol is, however, acceptable, and may be contained in the use according to the invention.

Suitable salts for the purpose of this invention and in each of the claimed uses are salts of the particular active substance with inorganic or organic acids and/or a sugar substitute such as saccharin, cyclamate or acesulfame. The hydrochloride is, however, particularly preferred.

The present invention also provides the use of O-demethyltramadol and/or its enantiomers, diastereomers, bases or salts of physiologically compatible acids for the production of a pharmaceutical preparation for the treatment of increased urinary urgency or urinary incontinence. It is in particular preferred to use (+)-O-demethyltramadol as a free base and/or in the form of physiologically compatible salts. In vivo, tramadol forms the metabolite O-demethyltramadol, which is likewise present as an enantiomer mixture. With regard to analgesic action, investigations have revealed that both the two tramadol enantiomers and the two enantiomers of the tramadol metabolites are involved in the analgesic action (*J. Pharmacol. Exptl. Ther.* 260, 275 (1992); *Arzneim. Forschung* 38, 877 (1988)).

Surprisingly, the racemate (O)-demethyltramadol also had a clear effect on bladder function even at low concentrations. More thorough investigation of the enantiomers revealed that (+)-O-demethyltramadol was apparently responsible for the entire effect on bladder function. EP 534 628 and WO 93/04675 disclose the production of O-demethyltramadol as a racemate or in enantiomer form. The (+)-O-demethyltramadol enantiomer is preferably produced using the process described in DE 196 01 744 C2.

When using (+)-O-demethyltramadol, it is not necessary, but is preferred, to use solely the (+)-O-demethyltramadol enantiomer. A smaller proportion of (−)-O-demethyltramadol relative to the (+)-O-demethyltramadol is, however, acceptable, and may be contained in the use according to the invention.

The present invention also provides the use of O-desmethyl-N-mono-desmethyltramadol and/or its enantiomers, in particular mixtures of its enantiomers or of a single enantiomer, diastereomers, bases or salts of physiologically compatible acids for the production of a pharmaceutical preparation for the treatment of increased urinary urgency or urinary incontinence. It is in particular preferred to use (+)-O-desmethyl-N-mono-desmethyltramadol as a free base and/or in the form of physiologically compatible salts.

O-desmethyl-N-mono-desmethyltramadol (referred to as M5 in some places in the following text and in the literature) is known as one of the in vivo metabolites of tramadol (1RS, 2RS)-2[(dimethylamino)methyl]-1-(3-methoxyphenyl) cyclohexanol (Lintz et al., *Arzneim.- Forsch./Drug Res.* 31(11), 1932–1943, 1981). M5 penetrates the blood-brain barrier to only a limited extent, as the effects on the central nervous system, for example analgesic effects, are distinctly less pronounced on intravenous administration than on intracerebroventricular administration. Surprisingly, the racemate O-demethyltramadol also had a clear effect on bladder function even at low concentrations. More thorough investigation of the enantiomers revealed that (+)-O-desmethyl-N-mono-desmethyltramadol was apparently responsible for the entire effect on bladder function.

When using (+)-O-desmethyl-N-mono-desmethyltramadol, it is not necessary, but is preferred, to use solely the (+)-O-desmethyl-N-mono-desmethyltramadol enantiomer. A smaller proportion of (−)-O-desmethyl-N-mono-desmethyltramadol relative to the (+)-O-desmethyl-N-mono-desmethyltramadol is, however, acceptable, and may be contained in the use according to the invention.

Although the compounds according to the invention exhibit only slight side effects, it may be advantageous, for example to avoid certain types of dependency, also to use morphine antagonists, in particular naloxone, naltrexone and/or levallorphan, in addition to (+)-tramadol, O-demethyltramadol or (+)-O-demethyltramadol, O-desmethyl-N-mono-desmethyltramadol or (+)-O-desmethyl-N-mono-desmethyltramadol.

The invention furthermore relates to pharmaceutical preparations for the treatment of increased urinary urgency or urinary incontinence, which preparations contain as active substance at least (+)-tramadol as a free base and/or in the form of physiologically compatible salts optionally together with additives and/or auxiliary substances or pharmaceutically acceptable excipients. In the corresponding pharmaceutical preparations it is not necessary, but is preferred, to use solely the (+)-tramadol enantiomer. A smaller proportion of (−)-tramadol relative to the (+)-tramadol is, however, acceptable, and may be contained in the pharmaceutical preparations according to the invention.

The invention also comprises pharmaceutical preparations for the treatment of increased urinary urgency or urinary incontinence, which preparations contain O-demethyltramadol and/or its enantiomers, diastereomers, bases or salts of physiologically compatible acids, in particular (+)-O-demethyltramadol as a free base and/or in the form of physiologically compatible salts optionally together with additives and/or auxiliary substances or pharmaceutically acceptable excipients. In the corresponding pharmaceutical preparations containing (+)-O-demethyltramadol, it is not necessary, but is preferred, to use solely the (+)-O-demethyltramadol enantiomer. A smaller proportion of (−)-O-demethyltramadol relative to (+)-O-demethyltramadol is, however, acceptable, and may be contained in the pharmaceutical preparations according to the invention.

The invention also comprises pharmaceutical preparations for the treatment of increased urinary urgency or urinary incontinence, which preparations contain as active substance at least O-desmethyl-N-mono-desmethyltramadol and/or its enantiomers, in particular mixtures of its enantiomers or a single enantiomer, diastereomers, bases or salts of physiologically compatible acids, in particular (+)-O-desmethyl-N-mono-desmethyltramadol as free base and/or in the form of physiologically compatible salts optionally together with additives and/or auxiliary substances. In the corresponding pharmaceutical preparations containing (+)-O-desmethyl-N-mono-desmethyltramadol, it is not necessary, but is preferred, to use solely the (+)-O-desmethyl-N-mono-desmethyltramadol enantiomer. A smaller proportion of (−)-O-desmethyl-N-mono-desmethyltramadol relative to the (+)-O-desmethyl-N-mono-desmethyltramadol is, however, acceptable, and may be contained in the pharmaceutical preparations according to the invention.

Suitable salts for the purposes of this invention and in each of the claimed uses are salts of the particular active substance with inorganic or organic acids and/or a sugar substitute such as saccharin, cyclamate or acesulfame. The hydrochloride is, however, particularly preferred.

Suitable additives and/or auxiliary substances for the purposes of this invention are any substances known to the person skilled in the art of obtaining pharmaceutical formulations. Selection of these auxiliary substances and the quantities thereof to be used depend upon whether the pharmaceutical preparation is to be administered orally, intravenously, intraperitoneally, intradermally, intramuscularly, intranasally, buccally or locally. Preparations in the form of tablets, chewable tablets, coated pills, capsules, granules, drops, elixirs or syrups are suitable for oral administration, while solutions, suspensions, readily reconstitutible dry preparations and sprays are suitable for parenteral, topical and inhalatory administration. Suppositories for rectal administration are another possibility. Examples of suitable percutaneous administration forms are use in a reservoir in dissolved form, in a carrier film or a plaster, optionally with added agents which promote skin penetration. Examples of auxiliary substances and additives for oral administration forms are suspending agents, lubricants, binders, fillers, mould release agents, optionally solvents, flavourings, sugar, in particular excipients, diluents, colorants, antioxidants etc. Waxes or fatty acid esters may, inter alia, be used for suppositories, while excipients, preservatives, suspending auxiliaries etc. may be used for parenteral administration forms. The quantities of active substance to be administered to patients vary as a function of patient weight, the route of administration and the severity of the condition. The compounds according to the invention may be released in a delayed manner from oral, rectal or percutaneous formulations. Such delayed release formulations, in particular in the form of a "once daily" preparation, which need be taken only once per day, are particularly preferred for the indication according to the invention.

Pharmaceutical preparations containing at least 0.05 to 90.0% of the active substance, in particular low active doses, are also preferred in order to avoid side effects or analgesic action.

Although the pharmaceutical preparations according to the invention exhibit only slight side effects, it may be advantageous, for example to avoid certain types of dependency, also to use morphine antagonists, in particular naloxone, naltrexone and/or levallorphan, in addition to (+)-tramadol, O-demethyltramadol or (+)-O-demethyltramadol, O-desmethyl-N-mono-desmethyltramadol or (+)-O-desmethyl-N-mono-desmethyltramadol.

The invention furthermore also relates to a process for the treatment of increased urinary urgency or urinary incontinence, in which process (+)-tramadol is used as a free base and/or in the form of physiologically compatible salts or corresponding processes in which O-demethyltramadol and/or its enantiomers, diastereomers, bases or salts of physiologically compatible acids, in particular (+)-O-demethyltramadol are/is used as a free base and/or in the form of physiologically compatible salts. A corresponding process, in which O-desmethyl-N-mono-desmethyltramadol and/or its enantiomers, diastereomers, bases or salts of physiologically compatible acids, in particular (+)-O-desmethyl-N-mono-desmethyltramadol is/are used as free base and/or in the form of physiologically compatible salts, is also encompassed by the invention.

The following Examples are intended to illustrate the invention, but without restricting the subject matter of the invention thereto.

EXAMPLES

Example 1

Cystometric Testing on Conscious, Virgin Rats

Cystometric testing was performed on virgin, female Sprague-Dawley rats using the method of Ishizuka et al. ((1997), *Naunyn-Schmiedeberg's Arch. Pharmacol.* 355: 787–793). Three days after implanting bladder and venous catheters, the animals were tested while conscious and freely mobile. The bladder catheter was connected to a pressure sensor and an injection pump. The animals were placed in metabolic cages, which allowed the volume of urine to be measured. Physiological saline was infused into the emptied bladder (10 ml/h) and bladder pressure and micturition volume were continuously recorded. After a stabilisation phase, a 20 minute phase was recorded which was characterised by normal, reproducible micturition cycles. Specifically, the following parameters were determined:

Micturition pressure (MP, maximum pressure during micturition), basal pressure (BP, lowest pressure during the filling phase), threshold pressure (TP, bladder pressure immediately before micturition), bladder capacity (BC, residual volume after prior micturition plus volume of infused solution during the filling phase), micturition volume (Mv, volume of voided urine) and residual volume (RV, bladder capacity minus micturition volume). Particular attention should be paid here to threshold pressure (TP), because any increase indicates an important therapeutic action in the indications according to the invention.

Example 2

Comparison of Racemic Tramadol, (+)-Tramadol and (−)-Tramadol

Once three reproducible micturition cycles had been recorded as an initial value, the test substances (tramadol, 10 mg/kg i.v.; (+)-tramadol, 5 mg/kg i.v.; (−)-tramadol, 5 mg/kg i.v.; vehicle=0.9% NaCl) were administered and their effect on cystometric parameters recorded for 90 to 120 minutes. At maximum action, the mean of three micturition cycles was determined and represented as a percentage change relative to the initial value (Table 1).

TABLE 1

Influence of tramadol and its enantiomers on cystometric parameters.

| | Micturition pressure [cm H₂O] | Threshold pressure [cm H₂O] | Basal pressure [cm H₂O] | Bladder capacity [ml] | Micturition volume [ml] | Residual volume [ml] |
|---|---|---|---|---|---|---|
| Tramadol 10.0 mg/kg i.v. (n = 9) | v: 74 ± 5<br>h: 66 ± 5<br>Diff.: −11% | v: 15.01 ± 1.32<br>h: 25.50 ± 2.40***<br>Diff.: +70% | v: 10.21 ± 1.03<br>h: 14.31 ± 1.89*<br>Diff.: +40% | v: 0.95 ± 0.06<br>h: 0.78 ± 0.08<br>Diff.: −18% | v: 0.85 ± 0.05<br>h: 1.13 ± 0.08**<br>Diff.: +33% | v: 0.10 ± 0.02<br>h: 0.05 ± 0.005<br>Diff.: −50% |
| (+)-Tramadol 5.0 mg/kg i.v. (n = 9) | v: 60 ± 4<br>h: 51 ± 7<br>Diff.: −15% | v: 8.0 ± 1.10<br>h: 19.20 ± 3.02**<br>Diff.: +53% | v: 4.23 ± 0.35<br>h: 6.46 ± 1.13*<br>Diff.: +140% | v: 0.92 ± 0.08<br>h: 0.90 ± 0.09<br>Diff.: −2% | v: 0.81 ± 0.07<br>h: 1.18 ± 0.12*<br>Diff.: +46% | v: 0.11 ± 0.02<br>h: 0.006 ± 0.003<br>Diff.: −95% |
| (−)-Tramadol 5.0 mg/kg i.v. (n = 10) | v: 69 ± 4<br>h: 59 ± 3*<br>Diff.: −15% | v: 7.32 ± 2.21<br>h: 7.10 ± 0.44<br>Diff.: −3% | v: 4.12 ± 0.40<br>h: 4.20 ± 0.30<br>Diff.: +2% | v: 1.19 ± 0.13<br>h: 1.10 ± 0.09*<br>Diff.: −8% | v: 1.07 ± 0.13<br>h: 1.01 ± 0.09<br>Diff.: −6% | v: 0.12 ± 0.01<br>h: 0.10 ± 0.02<br>Diff.: −17% |

Notes: The stated values are averages with standard deviation before (v) and after (h) administration of the test substance together with the difference (Diff.), the change relative to the initial value [%]; n corresponds to the number of tests; significance (Student T test): *p < 0.05, p < 0.01, *p < 0.001.

Tramadol (10 mg/kg i.v.) exhibited the expected effect in this case. A distinct rise in threshold pressure was observed. This indicates that tramadol racemate has a positive effect on bladder function, as was already known from WO 98/46216. In contrast, investigation of the two enantiomers (each at 5 mg/kg i.v.) revealed that only the (+)-enantiomer, but not the (−)-enantiomer, has an effect on bladder parameters. The effect of 5 mg/kg of tramadol in this case distinctly exceeds the effect of 10 mg/kg of racemic tramadol. With regard to threshold pressure, the action is observed even to be doubled. It may consequently be concluded that (+)-tramadol is the active component of the racemate and that (−)-tramadol in the racemate is probably not only inactive, but possibly even has an inhibitory effect.

It has thus been proven that (+)-tramadol has a distinctly better effect on bladder function than does racemic tramadol.

Example 3

Comparison of Racemic Tramadol, (+)-Tramadol and (+)-O-desmethyltramadol

In an analogous test according to Example 1, once three reproducible micturition cycles had been recorded as an initial value, racemic tramadol ((r)-tram) (1.0 and 5.0 mg/kg), (+)-tramadol ((+)-tram) (0.1, 0.3 and 0.5 mg/kg) and (+)-O-desmethyltramadol ((+)-M1) (0.1 and 0.5 mg/kg) in 0.9% NaCl as vehicle were administered i.v. and their effect on cystometric parameters recorded for 90 to 120 minutes. At maximum action, the mean of three micturition cycles was determined and represented as a percentage change relative to the initial value (Table 2). Some data from Table 1 are shown again for comparison purposes.

In addition to the previous test, the "inter-contraction interval", the period of time between micturition, was also measured in this test. The inter-contraction interval is also an important parameter for measuring the physiological effectiveness of a substance in treating urinary incontinence.

TABLE 2

Influence of tramadol and its enantiomers and metabolites on cystometric parameters.

| | Micturition pressure [cm H₂O] | Threshold pressure [cm H₂O] | Basal pressure [cm H₂O] | Bladder capacity [ml] | Micturition volume [ml] | Residual volume [ml] | Inter-contraction interval [min] |
|---|---|---|---|---|---|---|---|
| (r)-Tram 1.0 mg/kg i.v. (n = 6) | v: 94 ± 7<br>h: 85 ± 6*<br>Diff.: −10% | v: 14.0 ± 2.04<br>h: 21.03 ± 3.10***<br>Diff.: +50% | v: 9.02 ± 1.12<br>h: 11.34 ± 1.54*<br>Diff.: +26% | v: 0.84 ± 0.11<br>h: 0.82 ± 0.09<br>Diff.: −2% | v: 0.75 ± 0.09<br>h: 0.95 ± 0.08*<br>Diff.: +27% | v: 0.09 ± 0.02<br>h: 0.01 ± 0.005<br>Diff.: −89% | |
| (r)-Tram 5.0 mg/kg i.v. (n = 10) | v: 103 ± 10<br>h: 75 ± 10***<br>Diff.: −27% | v: 12.45 ± 1.411<br>h: 17.05 ± 2.33*<br>Diff.: +37% | v: 9.21 ± 1.35<br>h: 9.30 ± 2.10<br>Diff.: +1% | v: 0.87 ± 0.07<br>h: 0.92 ± 0.08<br>Diff.: +6% | v: 0.76 ± 0.06<br>h: 1.08 ± 0.09***<br>Diff.: +42% | v: 0.11 ± 0.02<br>h: 0.03 ± 0.01*<br>Diff.: −73% | Diff.: −11% |
| (r)-Tram♥ 10.0 mg/kg i.v. (n = 9) | v: 74 ± 5<br>h: 66 ± 5<br>Diff.: −11% | v: 15.01 ± 1.32<br>h: 25.50 ± 2.40***<br>Diff.: +70% | v: 10.21 ± 1.03<br>h: 14.31 ± 1.89*<br>Diff.: +40% | v: 0.95 ± 0.06<br>h: 0.78 ± 0.08<br>Diff.: −18% | v: 0.85 ± 0.05<br>h: 1.13 ± 0.08**<br>Diff.: +33% | v: 0.10 ± 0.02<br>h: 0.05 ± 0.005<br>Diff.: −50% | Diff.: −40% |
| (+)-Tram 0.1 mg/kg i.v. (n = 5) | v: 69 ± 11<br>h: 55 ± 8*<br>Diff.: −20% | v: 7.87 ± 1.51<br>h: 11.63 ± 1.05*<br>Diff.: +48% | v: 4.01 ± 0.57<br>h: 3.85 ± 0.46<br>Diff.: −4% | v: 0.91 ± 0.11<br>h: 1.07 ± 0.13*<br>Diff.: +18% | v: 0.75 ± 0.12<br>h: 0.80 ± 0.09<br>Diff.: +7% | v: 0.16 ± 0.01<br>h: 0.23 ± 0.07<br>Diff.: 44% | v: 5.35 ± 0.63<br>h: 7.13 ± 0.85*<br>Diff.: +33% |
| (+)-Tram 0.3 mg/kg i.v. (n = 8) | v: 71 ± 4<br>h: 60 ± 5<br>Diff.: −15% | v: 8.21 ± 0.42<br>h: 16.01 ± 1.63<br>Diff.: +95% | v: 4.50 ± 0.29<br>h: 4.95 ± 0.19<br>Diff.: +10% | v: 0.99 ± 0.08<br>h: 1.38 ± 0.14<br>Diff.: +39% | v: 0.86 ± 0.07<br>h: 0.97 ± 0.13<br>Diff.: +13% | v: 0.15 ± 0.01<br>h: 0.40 ± 0.04<br>Diff.: +167% | v: 6.06 ± 0.49<br>h: 7.21 ± 0.72*<br>Diff.: +19% |
| (+)-Tram 0.5 mg/kg i.v. (n = 5) | v: 73 ± 12<br>h: 57 ± 10*<br>Diff.: −22% | v: 7.85 ± 1.04<br>h: 15.0 ± 2.58*<br>Diff.: +91% | v: 4.16 ± 0.62<br>h: 4.70 ± 1.14<br>Diff.: +13% | v: 1.21 ± 0.06<br>h: 1.43 ± 0.11*<br>Diff.: +18% | v: 1.07 ± 0.06<br>h: 1.31 ± 0.12*<br>Diff.: +22% | v: 0.14 ± 0.03<br>h: 0.12 ± 0.002<br>Diff.: −14% | Diff.: +21% |

TABLE 2-continued

Influence of tramadol and its enantiomers and metabolites on cystometric parameters.

| | Micturition pressure [cm H$_2$O] | Threshold pressure [cm H$_2$O] | Basal pressure [cm H$_2$O] | Bladder capacity [ml] | Micturition volume [ml] | Residual volume [ml] | Inter-contraction interval [min] |
|---|---|---|---|---|---|---|---|
| (+)-Tram 5.0 mg/kg i.v. (n = 10) | v: 60 ± 4 h: 51 ± 7 Diff.: −15% | v: 8.0 ± 1.10 h: 19.20 ± 3.02** Diff.: +140% | v: 4.23 ± 0.35 h: 6.46 ± 1.13* Diff.: +53% | v: 0.92 ± 0.08 h: 0.90 ± 0.09 Diff.: −2% | v: 0.81 ± 0.07 h: 1.18 ± 0.12*** Diff.: +46% | v: 0.11 ± 0.02 h: 0.006 ± 0.003** Diff.: −95% | Diff.: +7% |
| (+)-M1 0.1 mg/kg i.v. (n = 5) | v: 90 ± 12 h: 70 ± 11 Diff.: −22% | v: 6.12 ± 0.51 h: 8.07 ± 0.97 Diff.: +32% | v: 3.62 ± 0.24 h: 3.87 ± 0.43 Diff.: +7% | v: 0.75 ± 0.08 h: 0.98 ± 0.06** Diff.: +31% | v: 0.64 ± 0.10 h: 0.95 ± 0.09* Diff.: +48% | v: 0.11 ± 0.02 h: 0.03 ± 0.02 Diff.: −73% | 4.20 ± 0.55 5.51 ± 0.52 Diff.: +31% |
| (+)-M1 0.5 mg/kg i.v. (n = 8) | v: 94 ± 10 h: 66 ± 10** Diff.: −30% | v: 7.44 ± 1.10 h: 15.34 ± 1.16*** Diff.: +106% | v: 3.91 ± 0.31 h: 4.90 ± 0.55* Diff.: +25% | v: 0.94 ± 0.08 h: 1.35 ± 0.11** Diff.: +44% | v: 0.85 ± 0.08 h: 1.28 ± 0.09*** Diff.: +51% | v: 0.09 ± 0.02 h: 0.06 ± 0.02 Diff.: −33% | 5.23 ± 0.45 7.63 ± 0.60** Diff.: +46% |

Notes: The stated values are averages with standard deviation before (v) and after (h) administration of the test substance together with the difference (Diff.), the change relative to the initial value [%]; n corresponds to the number of tests; significance (Student T test): *p < 0.05, p < 0.01, *p < 0.001. Values marked ♥ are repetitions from Example 2.

Overall, when evaluating effectiveness in urinary incontinence, particular value should be attached to threshold pressure (TP), bladder capacity (BC) and the inter-contraction interval (ICI). ®-Tram was as effective at (+)-tram only at considerably higher doses and, at the most effective dose (10 mg/kg), exhibited a distinct reduction in ICI. This latter phenomenon in particular is, however, an extremely unfavourable side effect in the treatment of urinary incontinence. Overall, (+)-tram is distinctly superior to racemic tramadol. (+)-Tram, for example, accordingly brings about a distinct increase in bladder capacity. (+)-O-desmethyltramadol is, however, apparently still better, both at 0.1 and, in particular, at 0.5 mg/kg i.v., a distinct rise in threshold pressure in particular being observed. Bladder capacity was also increased and the interval between micturition extended. O-desmethyltramadol, in particular (+)-O-desmethyltramadol has thus been proven to have a positive effect on bladder function which apparently distinctly surpasses that of racemic tramadol and, with regard to decisive parameters, even that of (+)-tramadol.

Example 4

Effectiveness of O-desmethyl-N-mono-desmethyltramadol, in Particular (+)-O-desmethyl-N-mono-desmethyltramadol In an analogous test according to Example 1, once three reproducible micturition cycles had been recorded as an initial value, (+)-O-desmethyl-N-mono-desmethyltramadol ((+)-M5) (10 mg/kg) in 0.9% NaCl as vehicle were administered i.v. and its effect on cystometric parameters recorded for 90 to 120 minutes. At maximum action, the mean of three micturition cycles was determined and represented as a percentage change relative to the initial value (Table 3). However, since it is not known whether M5 or (+)-M5 can pass through the blood-brain barrier and the effect may act centrally, 10 µg/kg were administered intrathecally (i.t.) (Table 3). In addition to Example 1, the "inter-contraction interval", the period of time between micturition, was measured in minutes.

TABLE 3

Influence of (+)-M5 on cystometric parameters.

| | Micturition pressure [cm H$_2$O] | Threshold pressure [cm H$_2$O] | Basal pressure [cm H$_2$O] | Bladder capacity [ml] | Micturition volume [ml] | Residual volume [ml] | Inter-contraction interval [min] |
|---|---|---|---|---|---|---|---|
| (+)-M5 10.0 mg/kg i.v. (n = 6) | v: 53 ± 4 h: 41 ± 3** Diff.: −23% | v: 7.13 ± 0.47 h: 12.08 ± 1.47* Diff.: +69% | v: 3.78 ± 0.26 h: 3.95 ± 0.35 Diff.: +4% | v: 0.88 ± 0.09 h: 0.72 ± 0.08* Diff.: −18% | v: 0.79 ± 0.09 h: 0.86 ± 0.10 Diff.: +9% | v: 0.08 ± 0.01 h: 0.01 ± 0.002** Diff.: −88% | v: 4.92 ± 0.53 h: 4.30 ± 0.47* Diff.: −12% |
| (+)-M5 10.0 µg/kg i.t. (n = 6) | v: 80 ± 9 h: 43 ± 6*** Diff.: −46% | v: 7.0 ± 0.93 h: 10.25 ± 1.01* Diff.: +46% | v: 4.68 ± 0.74 h: 4.25 ± 0.33 Diff.: −9% | v: 0.66 ± 0.05 h: 1.06 ± 0.06** Diff.: +61% | v: 0.53 ± 0.06 h: 0.72 ± 0.04* Diff.: +36% | v: 0.13 ± 0.01 h: 0.34 ± 0.04* Diff.: +162% | v: 3.78 ± 0.35 h: 5.22 ± 0.27** Diff.: +38% |

Notes: The stated values are averages with standard deviation before (v) and after (h) administration of the test substance together with the difference (Diff.), the change relative to the initial value [%]; n corresponds to the number of tests; significance (Student T test): *p < 0.05, p < 0.01, *p < 0.001.

(+)-O-desmethyl-N-mono-desmethyltramadol is also effective and, at 10.0 mg/kg i.v., is comparable with tramadol. A distinct rise in threshold pressure was observed, wherein the interval between micturition was not shortened with (+)-M5. (+)-M5 is also effective intrathecally and, in addition to an increase in threshold pressure, brings about distinct increases in bladder capacity and the interval between micturition. O-desmethyl-N-mono-desmethyltramadol, in particular (+)-O-desmethyl-N-mono-desmethyltramadol, has thus been proven to have a positive effect on bladder function.

The foregoing disclosure has been set forth merely to illustrate the invention and is not intended to be limiting. Since modifications of the disclosed embodiments incorporating the spirit and substance of the invention may occur to persons skilled in the art, the invention should be construed to broadly include everything within the scope of the appended claims and equivalents thereof.

What is claimed:

1. A method for the treatment of increased urinary urgency or urinary incontinence, the method comprising administering to a patient in need thereof an effective amount of a compound selected from the group consisting of (+)-tramadol, O-demethyltramadol, O-desmethyl-N-mono-desmethyltramadol, pharmaceutically acceptable salts thereof, and an enantiomer or diastereamer of O-demethyltramadol or O-desmethyl-N-mono-desmethyltramadol.

2. A method according to claim 1, wherein the pharmaceutically acceptable salt is a hydrochloride.

3. A method according to claim 1, wherein the compound is (+)-tramadol, or a pharmaceutically acceptable salt thereof.

4. A method according to claim 1, wherein the compound is O-demethyltramadol, or an enantiomer, diastereomer, or a pharmaceutically acceptable salt thereof.

5. A method according to claim 4, wherein compound is (+)-O-demethyltramadol or a pharmaceutically acceptable salt thereof.

6. A method according to claim 1, wherein the compound is O-desmethyl-N-mono-desmethyltramadol, or an enantiomer, diastereomer, or a pharmaceutically acceptable salt thereof.

7. A method according to claim 6, wherein the pharmaceutical composition comprises (+)-O-desmethyl-N-mono-desmethyltramadol or a pharmaceutically acceptable salt thereof.

8. A method according to claim 1, wherein the compound is administered in combination with a pharmaceutically acceptable excipient.

* * * * *